United States Patent [19]

Loev et al.

[11] Patent Number: 4,476,125

[45] Date of Patent: Oct. 9, 1984

[54] BENZOBISOXAZINETETRONES AND ANTI-ALLERGIC USE THEREOF

[75] Inventors: Bernard Loev, Scarsdale, N.Y.; Fu-Chih Huang, Boonton, N.J.

[73] Assignee: USV Pharmaceutical Corporation, Tarrytown, N.Y.

[21] Appl. No.: 478,394

[22] Filed: Mar. 24, 1983

[51] Int. Cl.³ .................. A61K 31/535; A61K 31/54; C07D 498/04; C07D 513/04

[52] U.S. Cl. .................. 424/246; 424/248.5; 424/248.51; 424/248.53; 424/248.56; 424/248.57; 544/34; 544/74; 544/101

[58] Field of Search .................. 544/34, 74, 101; 424/246, 248.5, 248.51, 248.53, 248.56, 248.57

[56] References Cited

U.S. PATENT DOCUMENTS 3,483,198 12/1969 Goldman .................. 544/34
3,746,707 7/1973 Gulbenk et al. .................. 544/101 X

*Primary Examiner*—Richard Raymond

[57] ABSTRACT

New benzobisoxazinetetrones having anti-allergic activity are described. These benzobisoxazinetetrones are represented by the following formula:

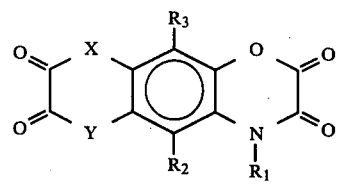

and pharmaceutically acceptable salts thereof, wherein:
X and Y are independently O, S, NH, N-alkyl or N-aryl;
$R_1$ is H, lower alkyl, aryl, aralkyl, heteroalkyl, alkoxyalkyl, aminoalkyl or carboxyalkyl;
$R_2$ and $R_3$ are independently H, OH, alkoxy, lower alkyl, aryl, aralkyl, halogen, trifluoromethyl, nitro, cyano, carboxy or sulfonamido useful in the treatment of allergies.

23 Claims, No Drawings

BENZOBISOXAZINETETRONES AND ANTI-ALLERGIC USE THEREOF

DESCRIPTION OF THE INVENTION

This invention relates to new chemical compounds and more particularly to new benzobisoxazinetetrones having anti-allergic activity when administered to a host topically, intranasally and the like. The benzobisoxazinetetrones of the present invention are represented by the following formula

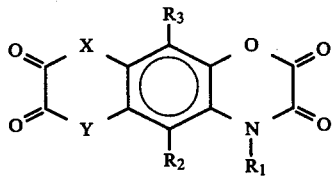

and pharmaceutically acceptable salts thereof, wherein:

X and Y are independently O, S, NH, N-alkyl, or N-aryl;

$R_1$ is H, lower alkyl, aryl, aralkyl, heteroalkyl, alkoxyalkyl, aminoalkyl or carboxyalkyl;

$R_2$ and $R_3$ are independently H, OH, alkoxy, lower alkyl, aryl, aralkyl, halogen, trifluoromethyl, nitro, cyano, carboxy or sulfonamido.

The alkyl group in lower alkyl, N-alkyl, aralkyl, heteroalkyl, alkoxyalkyl, aminoalkyl or carboxyalkyl contains 1 to 8 carbon atoms and may be branched or unbranched. Such groups include methyl, ethyl, propyl, isopropyl, butyl, isobutyl, amyl, isoamyl, pentyl, hexyl and the like.

The aryl group in aryl, N-aryl, aralkyl is preferably phenyl or naphthyl.

The halogen is F, Cl, Br or I.

The preferred compounds of the present invention are those in which: Y is O when X=N and X is O when Y=N; R and $R_1$ are independently H, alkyl, aryl or aralkyl; and $R_2$ and $R_3$ are independently H, alkyl, halogen, trifluoromethyl, nitro, cyano or carboxy.

The compounds of the present invention may be readily prepared by standard synthetic procedures from known starting materials and intermediates. The desired starting materials and intermediates can also be prepared from readily available materials using standard organic reactions or alternatively, some starting materials and intermediates may be purchased from chemical supply companies. The synthesis of all of the compounds disclosed and/or claimed will be easily understood by those skilled in the art when viewed by the teaching of this disclosure and the examples contained therein.

For illustration, a schematic procedure for making two compounds of the present invention follows:

Compound I, wherein $R=R_1=R_2=R_3=H$ and $Y=X=O$

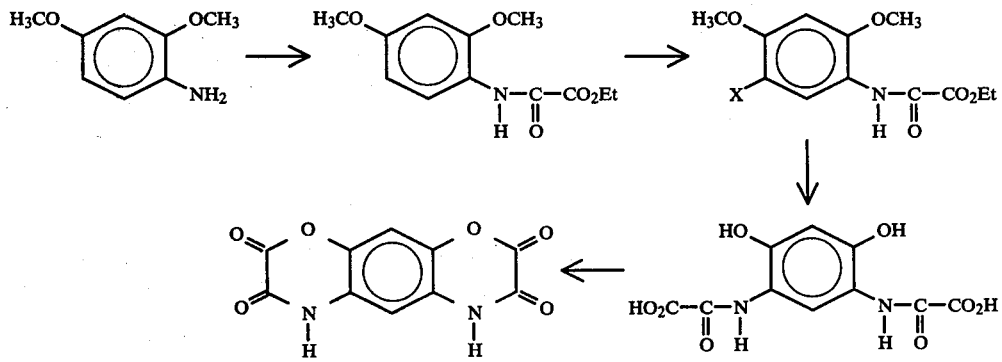

Compound II, wherein $R=R_1=R_2=R_3=H$ and $Y=X=O$

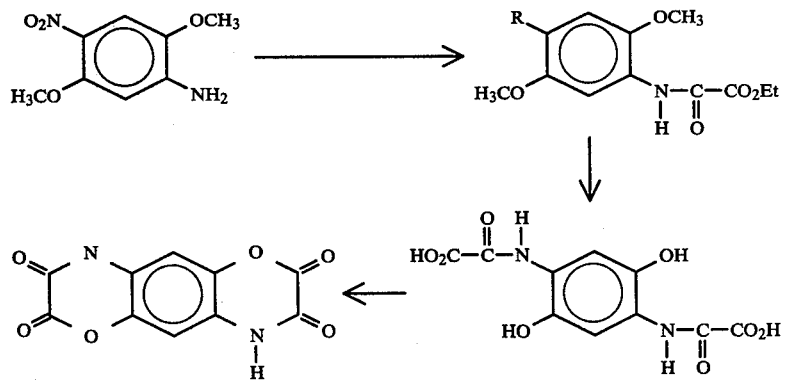

The invention will be fully illustrated in the examples that follow. These examples are given by way of illustration and are not to be considered as limiting.

EXAMPLE 1A

Ethyl N-(2,4-dimethoxyphenyl)oxanilate

To a mixture of 2,4-dimethoxyaniline (30.6 g, 0.199 mol) and triethylamine (50 ml) in 250 ml of methylene chloride was added ethyl oxalyl chloride (27.5 ml), 0.199 mol) dropwise over a period of 30 min at room temperature. After addition was completed, the reaction mixture was stirred for an additional 3 hrs. The organic solution was washed with water, dried and evaporated to give 40 g (59%) of off-white solid, m.p. 142°–144°. NMR (CDCl$_3$) 1.4 (t,3H), 3.8 (s,3H), 39 (s,3H), 4.38 (q,2H), 6.5 (q,2H), 8.3 (s,1H).

EXAMPLE 1B

Ethyl N-2,4-dimethoxy-5-nitrophenyl)oxanilate

The compound of Example 1A (25 g, 98.4 mmols) in 200 ml of methylene chloride and 200 ml of acetic acid was nitrated with 4 ml of fuming nitric acid over a period of 30 minutes. The reaction mixture was stirred at room temperature for 3 hrs. Filtration and recrystallization (ethyl acetate/hexane) gave 22 g (75%) of pale yellow solid, m.p. 197°–198°. NMR 1.41 (t,3H), 3.97 (s,3H), 4.04 (s,3H), 4.4 (q,2H), 6.55 (s,1H), 9 (s,2H), Anal. ($C_{12}H_{14}N_2O_7$) C, H, N.

EXAMPLE 1C

Ethyl N-(2,4-dimethoxy-5-aminophenyl)oxanilate

The compound of Example 1B (12 g) and 1.5 g of 5% pd/c in 300 ml of ethanol was hydrogenated at 40 psi overnight. Filtration followed by evaporation of solvent gave 10.5 of a yellow solid.

NMR (CDCl$_3$) 1.42 (t,3H), 3.88 (s,6H), 4.38 (q,2H), 6.48 (s,1H), 7.85 (s,1H).

This compound was used without further purification.

EXAMPLE 1D

Diethyl 2,4-dimethoxy-1,5-phenylenediamine-N,N'-bisoxanilate

To a solution of the aniline derivatives of Example 1C (21 g, 78.36 mmol) and triethyl amine (30 ml) in 300 ml of chloroform was added dropwise of ethyl oxalyl chloride (11.6 ml, 79 mmol) in 40 ml of methylene chloride over a period of 30 minutes. The reaction mixture was stirred for an additional 3 hours at room temperature. The organic solution was washed with water, 1N hydrochloric acid, and 5% sodium bicarbonate solution to give 2.7 g of light yellow solid. Recrystallization from ethanol gave 23 g (79.7%) of product, m.p. 183°–184°. NMR (CDCl$_3$) 1.4 (t,6H), 3.9 (s,6H), 4.38 (q,4H), 6.5 (s,1H), 9.18 (s,1H).

Anal. ($C_{16}H_{20}N_2O_8$) C, H, N.

EXAMPLE 1E 2,4-Dihydroxy-1,5-phenylenediamine-N,N'-bisoxanilic acid

A mixture of Example 1D (8 g) and 10 ml of borontribromide in 30 ml of methylene chloride was heated to reflux overnight. Excess boron tribromide was decomposed by water. The product was filtered and dried to give 4.3 g of the title compound as a yellow solid. This compound was used without further purification. NMR (DMSO-d$_6$) 6.57 (s,1H), 8.53 (s,1H).

EXAMPLE 1F

Benzo[1,2-b;5,4-b]-bis-[1,4]oxazine-2,3,7,8-tetrone

To a refluxing solution of the crude compound of Example 1E (4.5 g) in 150 ml of acetic acid was added dropwise a mixture of 4 g acetic anhydride in 10 ml of acetic over a period of 40 minutes. Refluxing was continued for 2 hours after the addition of acetic anhydride. The reaction mixture was filtered hot, and the solid product was washed well with methylene chloride to give 2.7 g of tan colored powder, m.p. >300°. NMR (DMSO-d$_6$) S 6.8 (S1H), 11.8 (S,2H).

Anal. ($C_{10}H_4N_2O_6\frac{1}{2}H_2O$) C, H, N.

EXAMPLE 2A

Ethyl N-(2,5-Dimethoxy-4-nitro-phenyl)oxanilate

To a mixture of compound 2,5-dimethoxy-4-nitroaniline (25 g, 0.126 mol), 130 ml of triethylamine (0.1262 mol) on 200 ml of methylene chloride and 40 ml of DMF was added dropwise a solution of ethyl oxalyl chloride (18.9 g, 0.139 mol) in 50 ml of methylene chloride at room temperature over a period of 30 minutes. After addition, the reaction mixture was concentrated and the residue was washed with water and filtered. Recrystallization from methylene chloride-hexane gave 36 g (95.6%) of product, m.p. 146°–147°. NMR (CDCl$_3$) 1.43 (t,3H), 3.97 (s,6H), 4.32 (q,2H), 7.53 (s,1H), 8.04 (s,1H).

Anal. ($C_{12}H_{14}N_2O_7$) C, H. N.

EXAMPLE 2B

Ethyl N-(2,5-dimethoxy-4-aminophenyl)oxanilate

A mixture of the nitro compound of Example 2A (30 g) and 3.6 g of 5% pd/c in 600 ml of ethanol was hydrogenated at 40 psi overnight. The reaction mixture was filtered and the catalyst was washed well with methylene chloride. The organic solution was evaporated to dryness to give 26 g of the title compound. This was used for the next reaction without further purification.

EXAMPLE 2C

Diethyl 2,5-dimethoxy-1,4-phenylenediamine-N,N'-bisoxanilate

Ethyl oxalyl chloride (15.5 g, 0.114 mol) in 30 ml of methylene chloride was added dropwise to a solution of the crude product (13b) obtained above (23 g, 91.3 mmol) and triethylamine (40 ml) in 300 ml of methylene chloride at room temperature over a period of 30 minutes. After stirring for an additional 2 hours the solvent was evaporated and the water (250 ml) was added to the residue. Filtration followed by recrystallization from ethanol gave 32.6 (97%) of the title compound as a cream yellow solid, m.p. 225°–226°. NMR (CDCl$_3$) 1.45(t,6H), 3.92(s,6H), 4.42(q,4H), 8.23(s,2H).

Anal. ($C_{16}H_{20}N_2O_8$)C,H,N.

EXAMPLE 2D 2,5-Dihydroxy-1,4-phenylenediamine-N,N'bisoxanilic acid

A mixture of compound of Example 2C (15 g, 40.7 mmol), and boron tribromide (10 ml) in 80 ml of methylene chloride was heated on an oil bath at 130°. The reaction was continued for 5 days. Excess boron tribromide was decomposed by water, and the reaction mixture was filtered and the solid product was dried to give 10.5 g of crude 2,5-dihydroxy-1,4-phenylenediamine-N,N'-bisoxanilic acid. This was used for the next reaction without further purification.

EXAMPLE 2E

Benzo(1,2-b;4,5-b)-bis-[1,4]oxazine-2,3,7,8-tetrone

Acetic anhydride (8.5 g) in 10 ml of acetic acid was added dropwise to a refluxing acetic acid solution (80 ml) containing 9 g of the product of Example 2D over a period of 2 hours. The reaction mixture was heated for an additional 2 hours and then filtered the solution hot. The product obtained (5.2 g, 66.4%), is analytically pure, m.p.>300°. NMR (DMSO-d₆) 6.83(s).

Anal. (C₁₀H₁₄N₂O₆H₂O)C,H,N.

According to the methods described in the previous examples the following compounds can be prepared from appropriate starting materials.

EXAMPLE 3

5-chloro-benzo[1,2-b; 5,4-b]-bis-[1,4]oxazine-2,3,7,8-tetrone

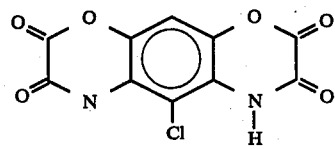

EXAMPLE 4

10-Methyl-benzo[1,2-b; 5,4-b]-bis-[1,4]oxazine-2,3,7,8-tetrone

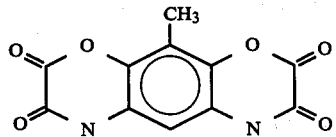

EXAMPLE 5

5-chloro-benzo[1,2-b; 4,5-b]-bis-[1,4]oxazine-2,3,7,8-tetrone

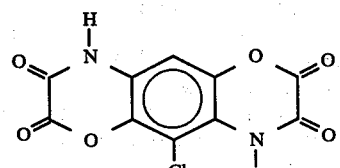

EXAMPLE 6

5-propyl-benzo[1,2-b; 4,5-b]-bis-[1,4]oxazine-2,3,7,8-tetrone

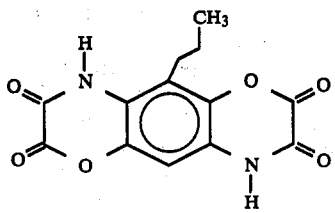

The compounds of the present invention are useful as intermediates for making benzo-bis-oxazoles. Further, the compounds of the present invention are useful as antiallergic agents as evidenced by their activity as blockers of histamine release from passively sensitized rat mast cells (RMC) and in the rat passive cutaneous test (PCA). A brief description of the test methods follow.

Rat Mast Cell (RMC) Studies—(Based on E. Kusner, B. Dabnick, D. F. Herzig, *J. Pharm. Exp., Ther.*, 1973, 184, 41.) Rat mast cells were passively sensitized in vitro with anti-ovalbumin serum. Following a 15 minute incubation, the spontaneous histamine release (SR) in the absence of antigent and AIR (in the presence of antigen) were measured fluorometrically with a Technicon Auto Analyzer ®. Test compounds were dissolved in DMSO (final concentration of DMSO was 0.1% and did not effect AIR).

Passive Cutaneous Anaphalixis in the Rat (Based on I. Mota, *Life Science*, 1963, F 465; and Z. Ovary and O. G. Bier, *Proc. Soc. Exp. Biol. and Med.*, 1952, 81, 584)—Male, Sprague Dawley rats were sensitized at dorsal sites by intradermal injection of syngeneic serum containing IgE anti-ovalbumin. Forty-eight hours later, groups of four rats were given either vehicle (1% methylcellulose) or graded does of compound. Either ten minutes after oral drug administration or five minutes after i.p. drug dosing, rats were challenged intravenously with antigen (oyalbumin) in 1% Evans blue dye. Thirty minutes after antigen challenge, the rats were sacrificed by cervical dislocations, the dorsal skins were reflected and blued wheal areas measured. Mean values±S.D. for wheal areas in control and drug-treated groups were detemined and compared statistically using Student's t-test. Oral time course studies were carried out using the same general passive cutaneous anaphalaxis (PCA) protocol except that an approximate or predicted ED₅₀ dose of compound was given at intervals ranging from 5 to 180 minutes prior to antigen challenge.

Representative results, obtained following to the above-described procedure, as shown in Table I.

TABLE I

| COMPOUND | SUBSTITUENTS | FORMULA | MP° C. | RMC $I_{50}$ ($\mu$M) | PCA % Inhibition 125 mg/kg p.o. |
|---|---|---|---|---|---|
| Example 1F | 6,7-NH—C(O)—C(O)—O— | C₁₀H₄N₂O₆ | >300 | 3 | 26% |
| Example 2E | 6,7-O—C(O)—C(O)—NH— | C₁₀H₄N₂O₆ | >300 | 1.2 | 42% |

The therapeutic compounds of the present invention may be administered alone or in combination with pharmaceutically acceptable carriers, the proportion of which is determined by the solubility and chemical nature of the compound, chosen route of administration such as topical, intranasal, oral and the like and standard pharmaceutical practice.

The physician will determine the dosage of the present therapeutic compounds which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a small quantity given parenterally. The compounds are useful in the same manner as other anti-allergic agents and the dosage level is of the same order of magnitude as is generally employed with these other therapeutic agents. The therapeutic dosage will generally be from 10 to 750 milligrams per day and higher although it may be administered in several different dosage units.

What is claimed is:

1. A compound of the formula

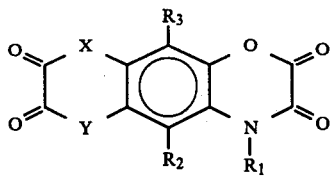

and pharmaceutically acceptable salts thereof, wherein:
X and Y are independently O, S, NH, N-alkyl, or N-aryl;
$R_1$ is H, lower alkyl, aryl, aralkyl, alkoxyalkyl, aminoalkyl or carboxyalkyl;
$R_2$ and $R_3$ are independently H, OH, alkoxy, lower alkyl, aryl, aralkyl, halogen, trifluoromethyl, nitro, cyano, carboxy or sulfonamido.

2. The compound of claim 1 wherein the alkyl group in lower alkyl, N-alkyl, aralkyl, alkoxyalkyl, aminoalkyl and carboxyalkyl contains from 1-8 carbon atoms and may be branched or unbranched.

3. The compound of claim 2 wherein said alkyl group is selected from the group consisting of methyl, ethyl, propyl, isopropyl, butyl, isobutyl, amyl, isoamyl, pentyl or hexyl.

4. The compound of claim 1 wherein the aryl group in aryl, N-aryl, and aralkyl is phenyl or naphthyl.

5. The compound of claim 1 wherein said halogen is F, Cl, Br or I.

6. A compound of the formula

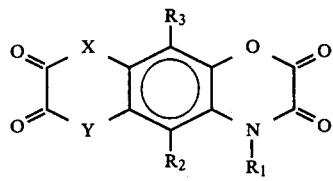

and pharmaceutically acceptable salts thereof, wherein:
X and Y are O;
$R_1$ is H, lower alkyl, aryl or aralkyl;
$R_2$ and $R_3$ are independently H, alkyl, halogen, trifluoromethyl, nitro, cyano or carboxy.

7. The compound of claim 6 wherein said alkyl in lower alkyl and aralkyl contains from 1-8 carbon atoms and may be branched or unbranched.

8. The compound of claim 7 wherein said alkyl is selected from the group consisting of methyl, ethyl, propyl, isopropyl, butyl, isobutyl, amyl, isoamyl, pentyl or hexyl.

9. The compound of claim 6 wherein said aryl in aryl and aralkyl is phenyl or naphthyl.

10. The compound of claim 6 wherein said halogen is F, Cl, Br or I.

11. An anti-allergic composition for administration to a mammal having allergic conditions comprising in combination with a pharmaceutically acceptable carrier an effective amount of an anti-allergic compound of the formula

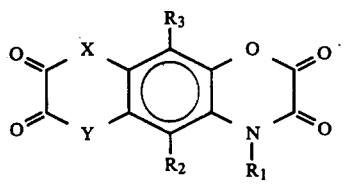

and pharmaceutically acceptable salts thereof, wherein:
X and Y are independently O, S, NH, N-alkyl, or N-aryl;
$R_1$ is H, lower alkyl, aryl, aralkyl, alkoxyalkyl, aminoalkyl or carboxyalkyl;
$R_2$ and $R_3$ are independently H, OH, alkoxy, lower alkyl, aryl, aralkyl, halogen, trifluoromethyl, nitro, cyano, carboxy or sulfonamido.

12. The anti-allergic composition of claim 11 wherein the alkyl group in lower alkyl, N-alkyl, aralkyl, alkoxyalkyl, aminoalkyl and carboxyalkyl contains from 1-8 carbon atoms and may be branched or unbranched.

13. The anti-allergic composition of claim 12 wherein said alkyl group is selected from the group consisting of methyl, ethyl, propyl, isopropyl, butyl, isobutyl, amyl, isoamyl, pentyl or hexyl.

14. The anti-allergic composition of claim 11 wherein the aryl group in aryl, N-aryl, and aralkyl is phenyl or naphthyl.

15. The anti-allergic composition of claim 11 wherein said halogen is F, Cl, Br or I.

16. An anti-allergic composition for administration to a mammal having allergic conditions comprising in combination with a pharmaceutically acceptable carrier an effective amount of an anti-allergic compound of the formula

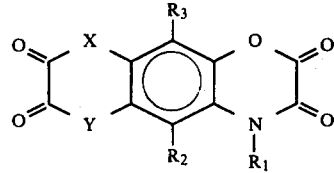

and pharmaceutically acceptable salts thereof, wherein:
X and Y are O;

$R_1$ is H, lower alkyl, aryl or aralkyl;

$R_2$ and $R_3$ are independently H, alkyl, halogen, trifluoromethyl, nitro, cyano or carboxy.

17. The anti-allergic composition of claim 16 wherein said alkyl in lower alkyl and aralkyl contains from 1–8 carbon atoms and may be branched or unbranched.

18. The anti-allergic composition of claim 17 wherein said alkyl is selected from the group consisting of methyl, ethyl, propyl, isopropyl, butyl, isobutyl, amyl, isoamyl, pentyl or hexyl.

19. The anti-allergic composition of claim 16 wherein said aryl in aryl and aralkyl is phenyl or naphthyl.

20. The anti-allergic composition of claim 16 wherein said halogen is F, Cl, Br or I.

21. A method of treating allergic conditions in a mammal by administering to said mammal an effective amount of the composition of claim 16.

22. The method of claim 21 wherein said administration is topical.

23. The method of claim 21 wherein said administration is intranasal.

* * * * *